US011820743B1

(12) United States Patent
Cui et al.

(10) Patent No.: US 11,820,743 B1
(45) Date of Patent: Nov. 21, 2023

(54) PURIFICATION METHOD AND DEVICE FOR CONTINUOUS DISTILLATION AND SEPARATION OF IBUPROFEN INTERMEDIATE RAW MATERIAL

(71) Applicant: Qingdao University of Science and Technology, Qingdao (CN)

(72) Inventors: Peizhe Cui, Qingdao (CN); Xin Li, Qingdao (CN); Yinglong Wang, Qingdao (CN); Zhaoyou Zhu, Qingdao (CN); Kaiguang Wang, Qingdao (CN); Jianguang Qi, Qingdao (CN); Limei Zhong, Qingdao (CN); Zhonghui Zheng, Qingdao (CN); Wenhui Xu, Qingdao (CN); Jianbo Jia, Qingdao (CN); Deping Du, Qingdao (CN)

(73) Assignee: Qingdao University Science and Technology, Shandong (CN)

(*) Notice: Subject to any disclaimer, the term of this patent is extended or adjusted under 35 U.S.C. 154(b) by 0 days.

(21) Appl. No.: 17/882,045

(22) Filed: Aug. 5, 2022

(30) Foreign Application Priority Data

May 30, 2022 (CN) .......................... 202210595575.7

(51) Int. Cl.
 *C07C 7/04* (2006.01)
 *C07C 15/06* (2006.01)
 *C07C 15/02* (2006.01)
(52) U.S. Cl.
 CPC .............. *C07C 7/04* (2013.01); *C07C 15/02* (2013.01); *C07C 15/06* (2013.01)

(58) Field of Classification Search
 None
 See application file for complete search history.

(56) References Cited

U.S. PATENT DOCUMENTS

| 3,316,315 A | * | 4/1967 | Jones | ........................ C07C 2/72 585/452 |
| 4,929,783 A | * | 5/1990 | Smith | ........................ C07C 2/72 585/467 |

* cited by examiner

*Primary Examiner* — Youngsul Jeong
*Assistant Examiner* — Alyssa L Cepluch
(74) *Attorney, Agent, or Firm* — Dominic A. Frisina

(57) ABSTRACT

The present disclosure belongs to the technical field of chemical separation and purification, and in particular relates to a purification method and device for continuous distillation and separation of an ibuprofen intermediate raw material. The purification method comprises the following steps: carrying out a primary distillation on synthetic liquid to obtain a primary material and recovered 4-methyl-1-pentene, then carrying out a second-stage distillation on the primary material to obtain a second-stage material and a recovered crude toluene product; and carrying out a third-stage distillation on the second-stage material to obtain isobutyl benzene and a recovered crude n-butylbenzene product. Embodiment results show that the purification method provided by the present disclosure is high in product recovery rate and high in product purity, the purity of isobutyl benzene is up to 99.99 wt %, the recovery rate is up to 99.9 wt %, the impurity content is not higher than 50 ppm.

9 Claims, 1 Drawing Sheet

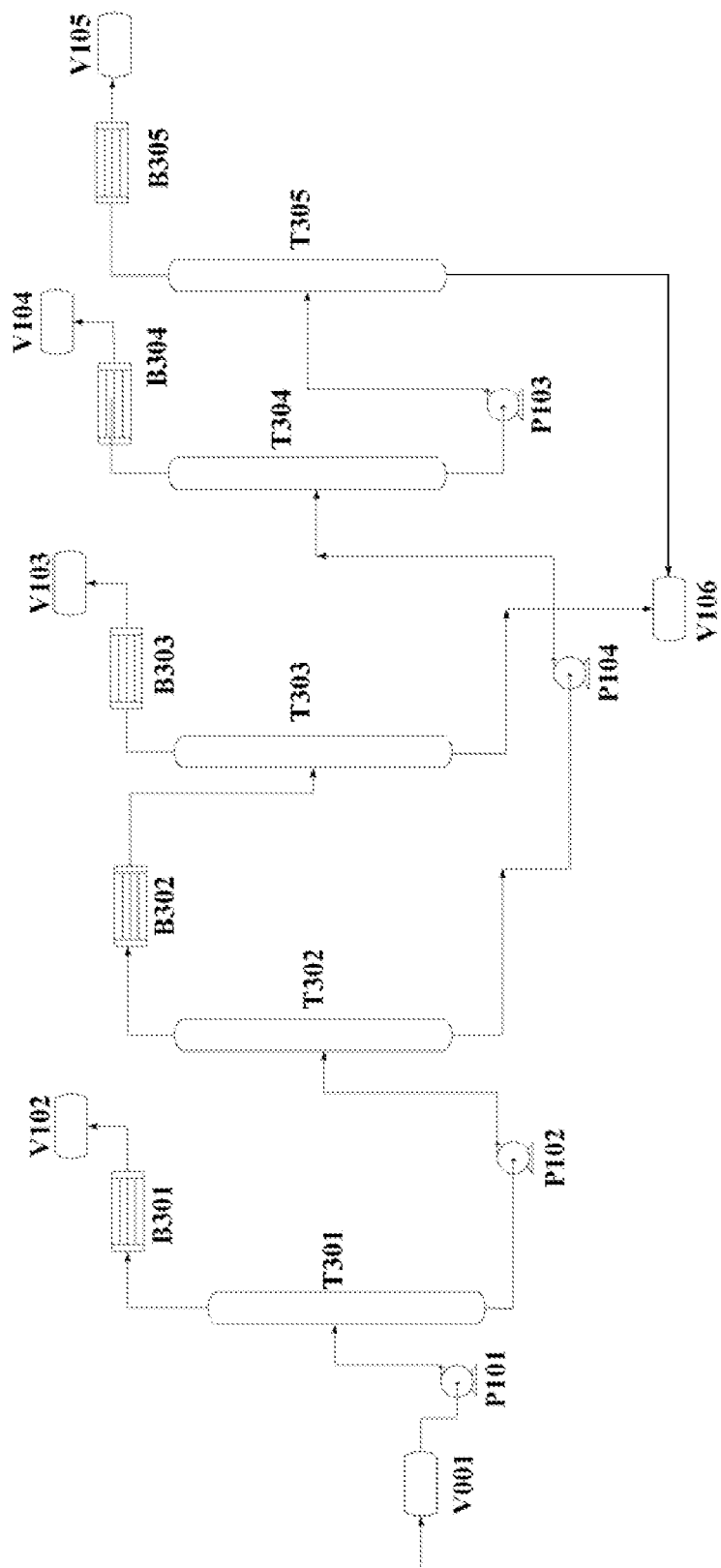

PURIFICATION METHOD AND DEVICE FOR CONTINUOUS DISTILLATION AND SEPARATION OF IBUPROFEN INTERMEDIATE RAW MATERIAL

CROSS REFERENCE TO RELATED APPLICATION

This patent application claims the benefit and priority of Chinese Patent Application No. 202210595575.7, filed on May 30, 2022, the disclosure of which is incorporated by reference herein in its entirety as part of the present application.

TECHNICAL FIELD

The present disclosure belongs to the technical field of chemical separation and purification, and in particular relates to a purification method and device for continuous distillation and separation of an ibuprofen intermediate raw material.

BACKGROUND ART

Ibuprofen is an anti-inflammatory, antipyretic and analgesic drug with good efficacy. The demand for ibuprofen intermediate raw materials in China is increasing, but in the domestic antipyretic-analgesic production industry, the production process for ibuprofen intermediates raw materials is backward, the product quality is not up to standard, energy consumption and cost are high. And due to various factors, the demand for the ibuprofen intermediate raw materials in China basically depends on import. Therefore, it is of great economic and strategic significance to strengthen the research on the refining process of ibuprofen intermediate raw materials, improve the process route for producing ibuprofen intermediate raw materials, enhance the quality of ibuprofen intermediate raw materials and reduce the production cost of ibuprofen intermediate raw materials.

At present, the commonly used ibuprofen intermediate raw materials include isobutyl benzene, p-isobutylacetophenone, etc. The isobutyl benzene is purified by adopting a fractional purification process of a batch distillation column, but the recovery rate of the isobutyl benzene in the fractional purification process of the batch distillation column is particularly low. A continuous distillation and purification system for unqualified chlorothalonil is disclosed by Chinese patent CN201822040975.3. In accordance with the purification system, a continuous distillation process is combined with a refining kettle to refine and purify the unqualified chlorothalonil, most of chlorothalonil in the unqualified chlorothalonil product is recovered. Although the hazardous wastes in the unqualified chlorothalonil product are effectively removed, the problem of low recovery rate also exists.

SUMMARY

An objective of the present disclosure is to provide a purification method and device for continuous distillation and separation of an ibuprofen intermediate raw material. In accordance with the method provided by the present disclosure, a recovery rate is up to 99.9 wt %, the product purity is up to 99.99 wt %, and the method has simple steps and high purification efficiency.

To achieve the objective, the present disclosure provided the following technical solutions:

A purification method for continuous distillation and separation of an ibuprofen intermediate raw material comprises the following steps:

(1) carrying out primary distillation on synthetic liquid to obtain a primary material and recovered 4-methyl-1-pentene, wherein the synthetic liquid comprises the following components: 50 wt % to 55 wt % of isobutyl benzene, 35 wt % to 38 wt % of toluene, 3 wt % to 5 wt % of 4-methyl-1-pentene, 3 wt % to 5 wt % of n-butylbenzene, and 2 wt % to 5 wt % of 1-ethyl-2-vinyl benzene;

(2) carrying out a second-stage distillation on the primary material to obtain a second-stage material and a recovered crude toluene product;

(3) carrying out a third-stage distillation on the second-stage material to obtain isobutyl benzene and a recovered crude n-butylbenzene product.

Preferably, the purification method further comprises the following steps:

(1) carrying out a fourth-stage distillation on the crude toluene product to obtain toluene and waste liquid;

(2) carrying out a fifth-stage distillation on the crude n-butylbenzene product to obtain n-butylbenzene and waste liquid.

Preferably, during primary distillation, the feeding temperature of the synthetic liquid is 25° C., the feeding pressure is 2 atm and a feeding flow rate is 900-5,000 kg/h.

Preferably, in the primary distillation, the pressure is 1 to 1.5 MPa, the column top temperature is 53 to 119° C. and the column bottom temperature is 115 to 132° C.

Preferably, in the second-stage distillation, the pressure is 0.015 to 0.020 MPa, the column top temperature is 53 to 119° C. and the column bottom temperature is 115 to 132° C.

Preferably, in the third-stage distillation, the pressure is 0.015 to 0.020 MPa, the column top temperature is 53 to 119° C. and the column bottom temperature is 115 to 132° C.

Preferably, in the fourth-stage distillation, the pressure is 0.07 to 1.00 MPa, the column top temperature is 53 to 119° C. and the column bottom temperature is 115 to 132° C.

Preferably, in the fifth-stage distillation, the pressure is 0.015 to 0.020 MPa, the column top temperature is 53 to 119° C. and the column bottom temperature is 115 to 132° C.

A device for the purification method of the technical solution is further provided, comprising:

a synthetic liquid storage tank (V001);

a 4-methyl-1-pentene removal column (T301) provided with a top outlet, a bottom outlet and a middle inlet, wherein the middle inlet is connected to an outlet of the synthetic liquid storage tank (V001);

a 4-methyl-1-pentene storage tank (V102), wherein an inlet of the 4-methyl-1-pentene storage tank (V102) is connected to the top outlet of the 4-methyl-1-pentene removal column (T301) via a first condenser (B301);

a toluene recovery column (T302) provided with a top outlet, a bottom outlet and a middle inlet, wherein the middle inlet is connected to the bottom outlet of the 4-methyl-1-pentene removal column (T301);

an isobutyl benzene column (T304) provided with a top outlet, a bottom outlet, and a middle inlet, wherein the middle inlet is connected to the bottom outlet of the toluene recovery column (T302); and an isobutyl benzene storage tank (V104), wherein an inlet of the isobutyl benzene storage tank (V104) is connected to the top outlet of the isobutyl benzene column (T304) via a fourth condenser (B304).

Preferably, the device further comprises:

a toluene column (T303) provided with a top outlet, a bottom outlet and a middle inlet, wherein the middle inlet is connected to the top outlet of the toluene recovery column (T302) via a second condenser (B302);

a toluene storage tank (V103), wherein an inlet of the toluene storage tank (V103) is connected to the top outlet of the toluene column (T303) via a third condenser (B303);

a high-boiling column (T305) provided with a top outlet, a bottom outlet and a middle inlet, wherein the middle inlet is connected to the bottom outlet of the isobutyl benzene column (T304);

a n-butylbenzene storage tank (V105), wherein an inlet of the n-butylbenzene storage tank (V105) is connected to the top outlet of the high-boiling column (T305) via a fifth condenser (B305); and a waste liquid storage tank (V106), wherein an inlet of the waste liquid storage tank (V106) is connected to the bottom outlet of the toluene column (T303), and the inlet of the waste liquid storage tank (V106) is connected to the bottom outlet of the high-boiling column (T305).

A purification method for continuous distillation and separation of an ibuprofen intermediate raw material is provided. The method comprises the following steps: carrying out a primary distillation on synthetic liquid to obtain a primary material and recovered 4-methyl-1-pentene, then carrying out a second-stage distillation on the primary material to obtain a second-stage material and a recovered crude toluene product; and carrying out a third-stage distillation on the second-stage material to obtain isobutyl benzene and a recovered crude n-butylbenzene product. The purification method provided by the present disclosure is high in product recovery rate and high in product purity, the purity of isobutyl benzene is up to 99.99 wt %, the recovery rate is up to 99.9 wt %, the impurity content is not higher than 50 ppm, and the problem of the separation of isobutyl benzene from 4-methyl-1-pentene, toluene and n-butylbenzene is solved. The method has simple steps, and has the advantages of low cost and low energy consumption.

The present disclosure further provides a device for the purification method of the solution. The device provided by the present disclosure is capable of carrying out effective separation and purification on the isobutyl benzene, is high in purification efficiency, simple in equipment structure, and suitable for industrial and continuous production. The purity of the obtained isobutyl benzene is up to 99.99 wt %, and the recovery rate is up to 99.9 wt %.

BRIEF DESCRIPTION OF THE DRAWINGS

To describe the technical solutions in the embodiments of the present disclosure or in the prior art more clearly, the following briefly introduces the accompanying drawings required for describing the embodiments. Apparently, the accompanying drawings in the following description show merely some embodiments of the present disclosure, and a person of ordinary skill in the art may still derive other drawings from these accompanying drawings without creative efforts.

The FIGURE is a schematic diagram of a device for purifying an ibuprofen intermediate raw material through continuous distillation and separation in accordance with the present disclosure. In the FIGURE, V001—synthetic liquid storage tank; V102—4-methyl-1-pentene storage tank; V103—toluene storage tank; V104—isobutyl benzene storage tank; V105—n-butylbenzene storage tank; V106—waste liquid storage tank; T301-4-methyl-1-pentene removal column; T302—toluene recovery column; T303—toluene column; T304—isobutyl benzene column; T305—high-boiling column; B301—first condenser; B302—second condenser; B303—third condenser; B304—fourth condenser; B305—fifth condenser; P101—first pump; P102—second pump; P103—third pump; P104—fourth pump.

DETAILED DESCRIPTION OF THE EMBODIMENTS

A purification method for continuous distillation and separation of an ibuprofen intermediate raw material comprises the following steps:

(1) carrying out primary distillation on synthetic liquid to obtain a primary material and recovered 4-methyl-1-pentene, wherein the synthetic liquid comprises the following components: 50 wt % to 55 wt % of isobutyl benzene, 35 wt % to 38 wt % of toluene, 3 wt % to 5 wt % of 4-methyl-1-pentene, 3 wt % to 5 wt % of n-butylbenzene and 2 wt % to 5 wt % of 1-ethyl-2-vinyl benzene;

(2) carrying out a second-stage distillation on the primary material to obtain a second-stage material and a recovered crude toluene product;

(3) carrying out a third-stage distillation on the second-stage material to obtain isobutyl benzene and a recovered crude n-butylbenzene product.

(The synthetic liquid is subjected to primary distillation to obtain the primary material and recovered 4-methyl-1-pentene, wherein the synthetic liquid comprises the following components: 50 wt % to 55 wt % of isobutyl benzene, 35 wt % to 38 wt % of toluene, 3 wt % to 5 wt % of 4-methyl-1-pentene, 3 wt % to 5 wt % of n-butylbenzene, and 2 wt % to 5 wt % of 1-ethyl-2-vinyl benzene. The ibuprofen intermediate raw material refers to a raw material for preparing an ibuprofen intermediate, i.e., isobutyl benzene. In accordance with the present disclosure, the synthetic liquid can be obtained by means of any process for producing the ibuprofen intermediate raw material by enterprises skilled in the art. In accordance with the present disclosure, the feeding temperature of the synthetic liquid is 25° C., the feeding pressure of the synthetic liquid is 2 atm, and a feeding flow rate of the synthetic liquid is 900 to 5,000 kg/h, more preferably 1,000 to 3,000 kg/h, further preferably 1,500 to 2,500 kg/h. The pressure in the primary distillation is preferably 1 MPa.

(After obtaining the primary material and the recovered 4-methyl-1-pentene, the primary material is subjected to a second-stage distillation to obtain a second-stage material and the recovered crude toluene product. In accordance with the present disclosure, the pressure in the second-stage distillation is preferably 0.015 MPa.

(After obtaining the second-stage material and the recovered crude toluene product, the second-stage material is subjected to a third-stage distillation to obtain isobutyl benzene and the recovered crude n-butylbenzene product. In accordance with the present disclosure, the pressure in the third-stage distillation is preferably 0.015 MPa.

(In accordance with the present disclosure, the purification method preferably further comprises the following steps: carrying out a fourth-stage distillation on the crude toluene product to obtain toluene and waste liquid; and carrying out a fifth-stage distillation on the crude n-butylbenzene product to obtain n-butylbenzene and waste liquid. The pressure in the fourth-stage distillation is preferably 0.07 MPa and the pressure in the fifth-stage distillation is preferably 0.015 MPa.

(In accordance with the present disclosure, reflux ratios of the primary distillation, the second-stage distillation, the third-stage distillation, the fourth-stage distillation and the fifth-stage distillation are independently and preferably 1 to 5; the reflux ratio of the primary distillation is more preferably 2 to 4 and is further preferably 3 to 4; the reflux ratio of the second-stage distillation is more preferably 1 to 4, further preferably 2 to 4; the reflux ratio of the third-stage distillation is more preferably 2 to 5, further preferably 2 to 4; the reflux ratio of the fourth-stage distillation is more preferably 2 to 4, further preferably 3 to 4; the reflux ratio of the fifth-stage distillation is more preferably 1 to 4, further preferably 3 to 4.

(A device for the purification method of the technical solution is further provided, comprising:

(a synthetic liquid storage tank (V001);

(a 4-methyl-1-pentene removal column (T301) provided with a top outlet, a bottom outlet and a middle inlet, wherein the middle inlet is connected to an outlet of the synthetic liquid storage tank (V001);

(a 4-methyl-1-pentene storage tank (V102), wherein an inlet of the 4-methyl-1-pentene storage tank (V102) is connected to the top outlet of the 4-methyl-1-pentene removal column (T301) via a first condenser (B301);

(a toluene recovery column (T302) provided with a top outlet, a bottom outlet and a middle inlet, wherein the middle inlet is connected to the bottom outlet of the 4-methyl-1-pentene removal column (T301);

an isobutyl benzene column (T304) provided with a top outlet, a bottom outlet, and a middle inlet, wherein the middle inlet is connected to the bottom outlet of the toluene recovery column (T302); and an isobutyl benzene storage tank (V104), wherein an inlet of the isobutyl benzene storage tank (V104) is connected to the top outlet of the isobutyl benzene column (T304) via a fourth condenser (B304).

In accordance the present disclosure, the device preferably further comprises:

a toluene column (T303) provided with a top outlet, a bottom outlet and a middle inlet, wherein the middle inlet is connected to the top outlet of the toluene recovery column (T302) via a second condenser (B302);

a toluene storage tank (V103), wherein an inlet of the toluene storage tank (V103) is connected to the top outlet of the toluene column (T303) via a third condenser (B303);

a high-boiling column (T305) provided with a top outlet, a bottom outlet and a middle inlet, wherein the middle inlet is connected to the bottom outlet of the isobutyl benzene column (T304);

a n-butylbenzene storage tank (V105), wherein an inlet of the n-butylbenzene storage tank (V105) is connected to the top outlet of the high-boiling column (T305) via a fifth condenser (B305); and a waste liquid storage tank (V106), wherein an inlet of the waste liquid storage tank (V106) is connected to the bottom outlet of the toluene column (T303), and the inlet of the waste liquid storage tank (V106) is connected to the bottom outlet of the high-boiling column (T305).

In accordance with the present disclosure, column diameters of the 4-methyl-1-pentene removal column T301, the toluene recovery column T302, the toluene column T303, the isobutyl benzene column T304 and the high-boiling column T305 are independently and preferably 400 to 900 mm, more preferably 500 to 800 mm, and further preferably 600 to 700 mm. The actual number of stages of the 4-methyl-1-pentene removal column T301 is 20 to 50, more preferably 25 to 45, and further preferably 30 to 40. The actual number of stages of the toluene recovery column T302 is preferably 50 to 70, more preferably 55 to 65, and further preferably 55 to 60. The actual number of stages of the toluene column T303 is preferably 30 to 60, more preferably 35 to 55, and further preferably 40 to 50. The actual number of stages of the isobutyl benzene column T304 is preferably 100 to 130, more preferably 105 to 125, and further preferably 110 to 120. The actual number of stages of the high-boiling column T305 is preferably 40 to 120, more preferably 60 to 100, and further preferably 80 to 90. The 4-methyl-1-pentene removal column T301, the toluene recovery column T302, the toluene column T303, the isobutyl benzene column T304 and the high-boiling column T305 preferably comprise one or more of a plate column and a packed column; and the plate column is preferably a sieve-plate column.

In accordance with the present disclosure, the middle inlet of the 4-methyl-1-pentene removal column T301 is preferably connected to the outlet of the synthetic liquid storage tank V001 via a first pump P101; the middle inlet of the 4-methyl-1-pentene removal column T301 is preferably the 8th to the 15th stages from top to bottom, more preferably the 9th to the 12th stages. The middle inlet of the toluene recovery column T302 is preferably connected to the bottom outlet of the 4-methyl-1-pentene removal column T301 via a second pump P102, and the middle inlet of the toluene recovery column T302 is preferably the 10th to the 15th stages from top to bottom, more preferably the 12th to the 14th stages. The middle inlet of the toluene column T303 is preferably connected to the top outlet of the toluene recovery column T302 via a second condenser B302, the middle inlet of the toluene column T303 is preferably the 10th to the 15th stages from top to bottom, more preferably the 11th to the 13th stages. The middle inlet of the isobutyl benzene column T304 is preferably connected to the bottom outlet of the toluene recovery column T302 via a fourth pump P104, and the middle inlet of the isobutyl benzene column T304 is preferably the 60th to the 85th stages from top to bottom, more preferably the 70th to the 80th stages. The middle inlet of the high-boiling column T305 is preferably connected to the bottom outlet of the isobutyl benzene column T304 via a third pump P103, and the middle inlet of the high-boiling column T305 is preferably the 40th to the 65th stages from top to bottom, more preferably the 45th to the 55th stages.

The FIGURE is a schematic diagram of a device for purifying an ibuprofen intermediate raw material through continuous distillation and separation in accordance with the present disclosure. In accordance with the present disclosure, when the device is used for carrying out continuous distillation, separation and purification on the ibuprofen intermediate raw material, the method preferably comprises the following steps: adding synthetic liquid into the synthetic liquid storage tank V001, then adding the synthetic liquid into the 4-methyl-1-pentene removal column T301 via the first pump P101; separating 4-methyl-1-pentene from the top of the 4-methyl-1-pentene removal column T301, and enabling the 4-methyl-1-pentene to enter the 4-methyl-1-pentene storage tank V102 via the first condenser B101; separating a primary material from the bottom of the 4-methyl-1-pentene removal column T301, and enabling the primary material to enter the toluene recovery column T302 via the second pump P102; separating toluene from the top of the toluene recovery column T302, and enabling the toluene to enter the toluene column T303 via the second condenser B302; separating a second-stage material from the bottom of the toluene recovery column T302, and enabling the second-stage material to enter the isobutyl benzene column T304 via the fourth pump P104; separating toluene from the top of the toluene column T303, and enabling the toluene to enter the toluene storage tank V103 via the third condenser B303; and separating waste liquid from the bottom of the column, and enabling the waste liquid to enter the waste liquid storage tank V106; separating isobutyl benzene from the top of the isobutyl benzene column T304, and enabling the isobutyl benzene to enter the isobutyl benzene storage tank V104 via a fourth condenser B304; separating a third-stage material from the bottom of the isobutyl benzene column T304, and enabling the third-stage material to enter the high-boiling column T305 via the third pump P103; separating n-butylbenzene from the column top of the high-boiling column T305, and enabling the n-butylbenzene to enter the n-butylbenzene storage tank V105 via a fifth condenser B305; and separating waste liquid from the column bottom of the high-boiling column T305, and enabling the waste liquid to enter the waste liquid storage tank V106.

To further describe the present disclosure, the following describes the technical solutions of the present disclosure in detail with reference to the accompanying drawings and embodiments, but the description cannot be construed as limiting the scope of protection of the present disclosure.

Embodiment 1

The feeding flow rate of the synthetic liquid is 900 kg/h, the feeding temperature is 25° C. and the feeding pressure is 2 atm, wherein the synthetic liquid contains 50 wt % of isobutyl benzene, 35 wt % of toluene, 5 wt % of 4-methyl-1-pentene, 5 wt % of n-butylbenzene and 5 wt % of 1-ethyl-2-vinyl benzene. The actual number of stages of the 4-methyl-1-pentene removal column T301 is 25, an optimal feeding position is the 13th stage from top to bottom, the reflux ratio is 1, and the pressure is 1 MPa; the actual number of stages of the toluene recovery column T302 is 50, an optimal feeding position is the 10th stage from top to bottom, the reflux ratio is 1.2, and the pressure is 0.015 MPa; the actual number of stages of the toluene column T303 is 44, an optimal feeding position is the 40th stage from top to bottom, the reflux ratio is 2.5, and the pressure is 0.07 MPa; the actual number of stages of the isobutyl benzene column T304 is 110, an optimal feeding position is the 75th stage from top to bottom, the reflux ratio is 4, and the pressure is 0.015 MPa; the actual number of stages of the high-boiling column T305 is 50, an optimal feeding position is the 47th stage from top to bottom, the reflux ratio is 3.5, and the pressure is 0.015 MPa. The finally obtained isobutyl benzene content is 99.997 wt %, the impurity content is 30 ppm, the recovery rate is 99.90 wt %, the purity of 4-methyl-1-pentene is 99.8 wt %, the purity of toluene is 99.9 wt %, and the purity of n-butylbenzene is 99.6 wt %.

Embodiment 2

The feeding flow rate of the synthetic liquid is 2,000 kg/h, the feeding temperature is 25° C., and the feeding pressure is 2 atm, wherein the synthetic liquid contains 55 wt % of isobutyl benzene, 35 wt % of toluene, 4 wt % of 4-methyl-1-pentene, 4 wt % of n-butylbenzene, and 2 wt % of 1-ethyl-2-vinyl benzene. The actual number of stages of the 4-methyl-1-pentene removal column T301 is 30, an optimal feeding position is the 15th stage from top to bottom, the reflux ratio is 1, and the pressure is 1 MPa; the actual number of stages of the toluene recovery column T302 is 60, an optimal feeding position is the 13th stage from top to bottom, the reflux ratio is 1.5, and the pressure is 0.01 MPa; the actual number of stages of the toluene column T303 is 42, an optimal feeding position is the 40th stage from top to bottom, the reflux ratio is 2.8 and the pressure is 0.015 MPa; the actual number of stages of the isobutyl benzene column T304 is 102, an optimal feeding position is the 82nd stage from top to bottom, the reflux ratio is 3.7, and the pressure is 0.015 MPa; the actual number of stages of the high-boiling column T305 is 48, an optimal feeding position is the 48th stage from top to bottom, the reflux ratio is 2.9, and the pressure is 0.015 MPa. The finally obtained isobutyl benzene content is 99.996 wt %, the impurity content is 40 ppm, the recovery rate is 99.92 wt %, the purity of 4-methyl-1-pentene is 99.8 wt %, the purity of toluene is 99.9 wt %, and the purity of n-butylbenzene is 99.6 wt %.

Embodiment 3

The feeding flow rate of the synthetic liquid is 5,000 kg/h, the feeding temperature is 25° C., and the feeding pressure is 2 atm, wherein the synthetic liquid contains 53 wt % of isobutyl benzene, 38 wt % of toluene, 3 wt % of 4-methyl-1-pentene, 3 wt % of n-butylbenzene, and 3 wt % of 1-ethyl-2-vinyl benzene. The actual number of stages of the 4-methyl-1-pentene removal column T301 is 22, an optimal feeding position is the 12th stage from top to bottom, the reflux ratio is 1.2, and the pressure is 1 MPa; the actual number of stages of the toluene recovery column T302 is 55, an optimal feeding position is the 15th stage from top to bottom, the reflux ratio is 1.8, and the pressure is 0.01 MPa; the actual number of stages of the toluene column T303 is 38, an optimal feeding position is the 35th stage from top to bottom, the reflux ratio is 2.1, and the pressure is 0.05 MPa; the actual number of stages of the isobutyl benzene column T304 is 120, an optimal feeding position is the 63rd stage from top to bottom, the reflux ratio is 3.9, and the pressure is 0.015 MPa; the actual number of stages of the high-boiling column T305 is 46, an optimal feeding position is the 43rd stage from top to bottom, the reflux ratio is 3.3, and the pressure is 0.07 MPa. The finally obtained isobutyl benzene content is 99.995 wt %, the impurity content is 50 ppm, the recovery rate is 99.94 wt %, the purity of 4-methyl-1-pentene is 99.8 wt %, the purity of toluene is 99.9 wt %, and the purity of n-butylbenzene is 99.6 wt %.

It can be known from the embodiments above that the purification method provided by the present disclosure is high in product recovery rate and high in product purity, the purity of isobutyl benzene is up to 99.99 wt %, the recovery rate is up to 99.9 wt %, the impurity content is not higher than 50 ppm, the purity of 4-methyl-1-pentene is up to 99.8 wt %, the purity of methylbenzene is up to 99.9 wt %, the purity of n-butylbenzene is up to wt %, and the method has simple steps, high purification efficiency, simple equipment structure and has the advantages of low cost and low energy consumption.

The described embodiments describing the present disclosure in detail are merely a part rather than all of the embodiments of the present disclosure. All other embodiments obtained based on the embodiments of the present disclosure without creative efforts shall fall within the scope of protection of the present disclosure.

What is claimed is:
1. A purification method for continuous distillation and separation of an ibuprofen intermediate raw material, comprising the following steps:
   (1) carrying out a primary distillation on a synthetic liquid to obtain a primary material and a recovered 4-methyl-

1-pentene product, wherein the synthetic liquid comprises the following components: 50 wt % to 55 wt % of isobutyl benzene, 35 wt % to 38 wt % of toluene, 3 wt % to 5 wt % of 4-methyl-1-pentene, 3 wt % to 5 wt % of n-butylbenzene, and 2 wt % to 5 wt % of 1-ethyl-2-vinyl benzene; wherein the primary material comprises isobutyl benzene, toluene, n-butylbenzene, and 1-ethyl-2-vinyl benzene;

(2) carrying out a second-stage distillation on the primary material to obtain a second-stage material and a recovered crude toluene product, wherein the second-stage material comprises isobutyl benzene, n-butylbenzene, and 1-ethyl-2-vinyl benzene; and (3) carrying out a third-stage distillation on the second-stage material to obtain a recovered isobutyl benzene product as the ibuprofen intermediate raw material and a recovered crude n-butylbenzene product.

2. The purification method according to claim 1, further comprising the following steps:

(4) carrying out a fourth-stage distillation on the crude toluene product to obtain a recovered toluene product and a first waste liquid; and (5) carrying out a fifth-stage distillation on the crude n-butylbenzene product to obtain a recovered n-butylbenzene product and a second waste liquid.

3. The purification method according to claim 1, wherein during the primary distillation, a feeding temperature of the synthetic liquid is 25° C., a feeding pressure is 0.203 MPa, and a feeding flow rate is 900-5,000 kg/h.

4. The purification method according to claim 1, wherein during the primary distillation, a pressure is 1 to 1.5 MPa, a column top temperature is 53 to 119° C., and a column bottom temperature is 115 to 132° C.

5. The purification method according to claim 1, wherein during the second-stage distillation, a pressure is 0.015 to 0.020 MPa, a column top temperature is 53 to 119° C., and a column bottom temperature is 115 to 132° C.

6. The purification method according to claim 1, wherein during the third-stage distillation, a pressure is 0.015 to 0.020 MPa, the column top temperature is 53 to 119° C., and a column bottom temperature is 115 to 132° C.

7. The purification method according to claim 2, wherein during the fourth-stage distillation, a pressure is 0.07 to 1.00 MPa, a column top temperature is 53 to 119° C., and a column bottom temperature is 115 to 132° C.

8. The purification method according to claim 2, wherein during the fifth-stage distillation, a pressure is 0.015 to 0.020 MPa, a column top temperature is 53 to 119° C., and a column bottom temperature is 115 to 132° C.

9. The purification method according to claim 3, wherein during the primary distillation, a pressure is 1 to 1.5 MPa, a column top temperature is 53 to 119° C., and a column bottom temperature is 115 to 132° C.

\* \* \* \* \*